(12) United States Patent
Boettger et al.

(10) Patent No.: US 9,375,184 B2
(45) Date of Patent: Jun. 28, 2016

(54) SYSTEM AND METHOD FOR PREDICTION OF RESPIRATORY MOTION FROM 3D THORACIC IMAGES

(71) Applicants: Siemens Corporation, Iselin, NJ (US); Siemens Aktiengesellschaft, Munich (DE); Siemens plc, Camberley (GB); University of Iowa, Iowa City, IA (US)

(72) Inventors: Thomas Boettger, Erlangen (DE); Francois Carnis, Antony (FR); Dorin Comaniciu, Princeton Junction, NJ (US); Jerome Declerck, Oxford (GB); Bernhard Fuerst, Angerberg (AT); Ali Kamen, Skillman, NJ (US); Tommaso Mansi, Plainsboro, NJ (US); Jingdan Zhang, Bellevue, WA (US)

(73) Assignees: Technische Universität München, München (DE); Siemens Aktiengesellschaft, München (DE); Siemens Corporation, Iselin, NJ (US); Siemens Healthcare GmbH, Erlangen (DE)

( * ) Notice: Subject to any disclaimer, the term of this patent is extended or adjusted under 35 U.S.C. 154(b) by 0 days.

(21) Appl. No.: 14/467,246

(22) Filed: Aug. 25, 2014

(65) Prior Publication Data
US 2015/0073765 A1 Mar. 12, 2015

Related U.S. Application Data

(60) Provisional application No. 61/876,877, filed on Sep. 12, 2013.

(51) Int. Cl.
*G06K 9/00* (2006.01)
*A61B 5/00* (2006.01)
*A61B 5/113* (2006.01)
*A61B 5/11* (2006.01)
*G06F 19/00* (2011.01)
*G06T 7/20* (2006.01)

(52) U.S. Cl.
CPC .............. *A61B 5/7275* (2013.01); *A61B 5/113* (2013.01); *A61B 5/1128* (2013.01); *G06F 19/3437* (2013.01); *G06T 7/2046* (2013.01); *G06T 2207/10072* (2013.01); *G06T 2207/30061* (2013.01)

(58) Field of Classification Search
USPC ................................................. 382/128–134
See application file for complete search history.

(56) References Cited

U.S. PATENT DOCUMENTS

| | | | | |
|---|---|---|---|---|
| 6,690,965 | B1 * | 2/2004 | Riaziat | A61B 6/463 378/62 |
| 6,937,696 | B1 * | 8/2005 | Mostafavi | A61B 5/7292 378/65 |
| 7,620,146 | B2 * | 11/2009 | Mostafavi | A61B 6/4441 378/62 |
| 8,170,312 | B2 | 5/2012 | Chen et al. | |

(Continued)

*Primary Examiner* — Alex Liew

(57) ABSTRACT

A method and system for prediction of respiratory motion from 3D thoracic images is disclosed. A patient-specific anatomical model of the respiratory system is generated from 3D thoracic images of a patient. The patient-specific anatomical model of the respiratory system is deformed using a biomechanical model. The biomechanical model is personalized for the patient by estimating a patient-specific thoracic pressure force field to drive the biomechanical model. Respiratory motion of the patient is predicted using the personalized biomechanical model driven by the patient-specific thoracic pressure force field.

37 Claims, 9 Drawing Sheets

(56) References Cited

U.S. PATENT DOCUMENTS

| | | |
|---|---|---|
| 8,233,688 B2 | 7/2012 | Soubelet et al. |
| 8,487,616 B2 | 7/2013 | Burger |
| 8,824,757 B2 | 9/2014 | Kolthammer et al. |
| 2004/0254492 A1* | 12/2004 | Zhang ............... A61B 5/1135 600/538 |
| 2004/0254773 A1* | 12/2004 | Zhang ............... A61B 5/1135 703/11 |
| 2007/0231779 A1* | 10/2007 | Santhanam ............ G09B 23/28 434/262 |
| 2008/0058657 A1* | 3/2008 | Schwartz ........... A61B 5/04085 600/508 |
| 2008/0123927 A1* | 5/2008 | Miga ..................... A61B 19/52 382/131 |
| 2010/0208957 A1 | 8/2010 | Chen et al. |
| 2011/0009761 A1 | 1/2011 | Ruan et al. |
| 2011/0164035 A1 | 7/2011 | Liao et al. |
| 2011/0275933 A1 | 11/2011 | Dey et al. |
| 2012/0230572 A1 | 9/2012 | Kohlberger et al. |
| 2012/0319685 A1 | 12/2012 | Burger |
| 2013/0303898 A1 | 11/2013 | Kinahan et al. |
| 2015/0073765 A1* | 3/2015 | Boettger ............. A61B 5/7275 703/11 |

\* cited by examiner

SYSTEM AND METHOD FOR PREDICTION OF RESPIRATORY MOTION FROM 3D THORACIC IMAGES

This application claims the benefit of U.S. Provisional Application No. 61/876,877, filed Sep. 12, 2013, the disclosure of which is herein incorporated by reference in its entirety.

The invention described was supported by National Institute of Health Award Number U01CA140206 from the National Cancer Institute.

BACKGROUND OF THE INVENTION

The present invention relates to prediction of respiratory motion from 3D thoracic images and more particularly to predicting deformation of the lungs and surrounding organs during respiration based on thoracic images for improved image reconstruction.

Medical imaging and non-invasive interventions often suffer from complications caused by respiratory motion, which is a source of artifacts in images and makes it difficult to correctly determine the shape, size, and position of organs or lesions, such as lung tumors. The respiratory motion is complex, as the lungs do not just compress and deform, but also slide along the thoracic cavity. This behavior is enabled by the pleura, which is filled with a serous fluid and does not change its volume during respiration, hence maintaining the lung and the thoracic cavity. The anatomical properties of the pleura allow nearly friction free sliding of the lungs and diaphragm along the thoracic cavity. The motion is caused by two major groups of muscles: the diaphragm and the intercostal muscles. The contraction of these muscles enlarges the thoracic cavity and indirectly leads to an increase in lung volume.

Respiratory motion is required in a multitude of applications, like image reconstruction or therapy delivery. Yet, because of the complexity in the respiratory motion, accurate estimation of 3D lung deformation is extremely challenging. Lung deformation is typically approximated by one- or multi-dimensional signals from devices such as spirometers, abdominal pressure belts, external markers, or imaging modalities. These surrogate signals partially reflect the complex nature of lung deformation during a respiratory cycle. For image acquisition, for instance, a 4D computed tomography (CT) data set is compounded by image segments sorted and combined either based on the amplitude or the phase-angle of a respiratory surrogate, where the signal is assumed to be periodic. However, difficulties arise when the breathing pattern changes, which results in a non-periodic surrogate signal and causes imaging artifacts due to the combination of different breathing states. In a second approach, images are acquired at a specific instance of the respiratory cycle by triggering the imaging modality according to the surrogate signal. This is referred to as gating and is commonly used for nuclear imaging, such as positron emission tomography (PET). In radiotherapy, gating is typically used only to apply the ionizing radiation during pre-defined respiratory states.

Both approaches have drawbacks, such as the increase in radiation dose to achieve oversampling, or the increase of treatment or imaging time. Furthermore, for imaging, interpolation due to the lack of information between respiratory phases can cause step artifacts. Therefore, a continuous approximation of respiratory motion is necessary.

BRIEF SUMMARY OF THE INVENTION

The present invention provides a method and system for predicting respiratory motion from 3D thoracic images. Embodiments of the present invention utilize a patient-specific, generative model of the respiratory system estimated from two 3D thoracic images, such as computed tomography (CT) or magnetic resonance (MR) images. Embodiments of the present invention utilize a model that relies on a pressure force field estimated from two images at different instants in the respiratory cycle to drive the lung motion. As the model is generative, it can be used to predict the 3D respiratory motion for different respiratory patterns by modulating the pressure force field. As such, embodiments of the present invention can predict the lung position at any time of the respiratory cycle, and thus can provide a 3D surrogate for improved image reconstruction or therapy delivery.

In one embodiment of the present invention, a patient-specific anatomical model of the respiratory system is generated from a 3D thoracic image of a patient. The patient-specific anatomical model of the respiratory system is deformed using a biomechanical model. The biomechanical model is personalized for the patient by estimating a patient-specific thoracic pressure force field to drive the biomechanical model. Respiratory motion of the patient is predicted using the personalized biomechanical model driven by the patient-specific thoracic pressure force field.

These and other advantages of the invention will be apparent to those of ordinary skill in the art by reference to the following detailed description and the accompanying drawings.

DETAILED DESCRIPTION

The present invention relates to prediction of respiratory motion from 3D thoracic images. Embodiments of the present invention are described herein to give a visual understanding of the methods for predicting respiratory motion. A digital image is often composed of digital representations of one or more objects (or shapes). The digital representation of an object is often described herein in terms of identifying and manipulating the objects. Such manipulations are virtual manipulations accomplished in the memory or other circuitry/hardware of a computer system. Accordingly, is to be understood that embodiments of the present invention may be performed within a computer system using data stored within the computer system.

Figure 1:
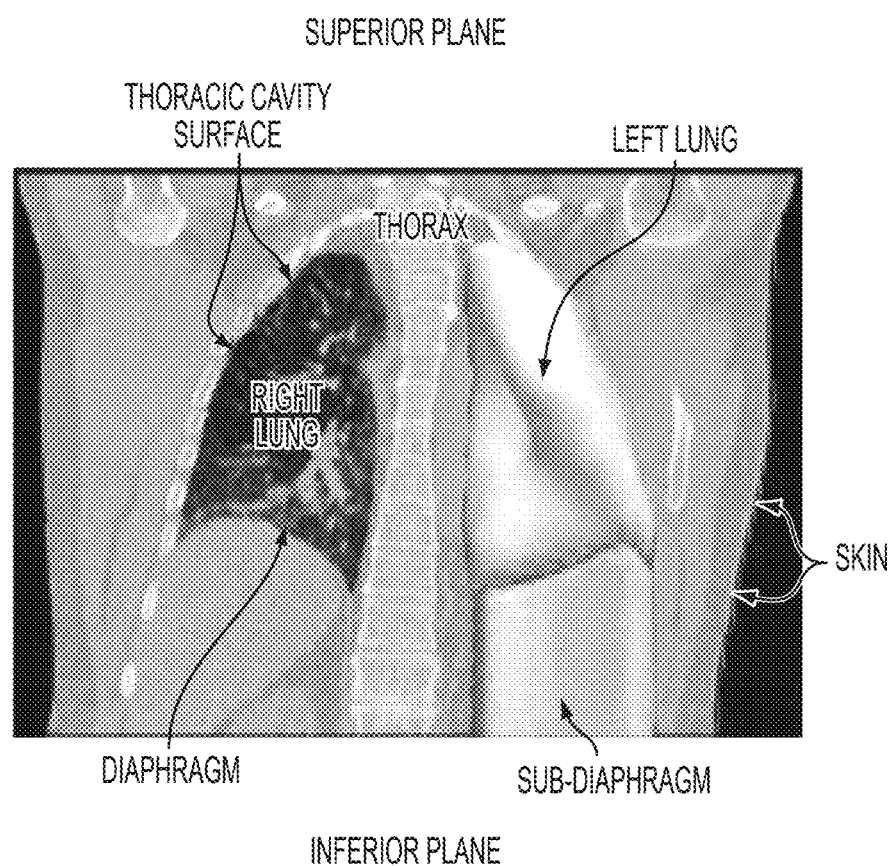
FIG. 1 is a computed tomography (CT) image showing the respiratory system of a patient.

FIG. 1 is a computed tomography (CT) image showing the respiratory system of a patient. Respiratory motion is complex, as the lungs do not just compress and deform, but also slide along the thoracic cavity. The diaphragm and intercostal muscles expand the thoracic cavity to inflate the lung. The pleura (not visible in the CT slice of FIG. 1) keeps the lung in close proximity to the thoracic cavity surface. Both the lungs and diaphragm can slide along the rib cage during respiration, nearly free of friction.

Various motion models have been proposed to estimate or predict the motion of the lungs, liver, or other organs during breathing. Image-based approaches for motion compensation typically define an image-based model by performing registration between images at different respiratory phases, resulting in a description of the observed motion using deformation fields. However, image-based methods are typically restricted to normal breathing patterns, with lower predictive power and versatility in patients, as the deformation fields used for prediction are based on observations and new motion models are difficult to estimate. Biomechanical-based methods for motion compensation aim to mimic the physiology, which makes the model generative and allows for prediction of the respiratory motion based on a surrogate signal. However, biomechanical-based approaches typically base the driving force of lung deformation on patient images, for example, by projecting triangulated surface nodes of the lung at the inhale respiratory phase onto the surface of the lung at the exhale respiratory phase, and deforming the lung accordingly. In this framework, the deformation is constrained by the limiting geometry, not by the actual forces acting on the lungs. The model then deforms under consideration of generalized or assumed tissue properties. As a result, such biomechanical-based approaches still rely on 4D image data to drive the simulation, which makes it difficult to predict respiratory motion when unexpected changes in breathing patterns appear.

Embodiments of the present invention provide a patient-specific, generative model of the respiratory system estimated from 3D or 4D images, such as 4D CT or MR images. Contrary to typical biomechanical-based methods, the generative computational motion model used in embodiments of the present invention does not rely on image data directly to drive the simulations, but instead is controlled by a pressure force field estimated from two images at different instants in the respiratory cycle. As the model is generative, it can predict 3D respiratory motion for different respiratory patterns by modulating the pressure force field. As such, embodiments of the present invention can be used to predict the lung position at any time of the respiratory cycle, and thus to constitute a 3D surrogate for improved image reconstruction.

According to an embodiment of the present invention, the driving force of the computational motion model of the respiratory system is defined by a patient-specific thoracic and diaphragmatic pressure distribution. This pressure force reflects muscular forces applied on the lung surface. Furthermore, embodiments of the present invention utilize a thorax/diaphragm/lung interaction model which is designed to closely reflect the pleura's behavior, keeping the lungs and thorax attached while allowing nearly friction-free movement. Embodiments of the present invention generate a computational motion model of the respiratory system that is generative, predictive, and patient-specific. According to an embodiment of the present invention, a detailed 3D anatomical model of the thoracic organs including, but not limited to, the lungs, thorax, airways, heart, and sub-diaphragm is generated from medical images, a patient-specific biomechanical model of the respiratory system is estimated that is driven by a thoracic pressure force field, a patient-specific thoracic pressure force field is estimated from dynamic thoracic images, respiratory motion is predicted by modulating the thoracic pressure force field, manually or in correlation with a surrogate signal, and a 3D+time map of respiratory deformation is generated. The 3D+time map can then be used for image reconstruction or therapy delivery.

Figure 2:
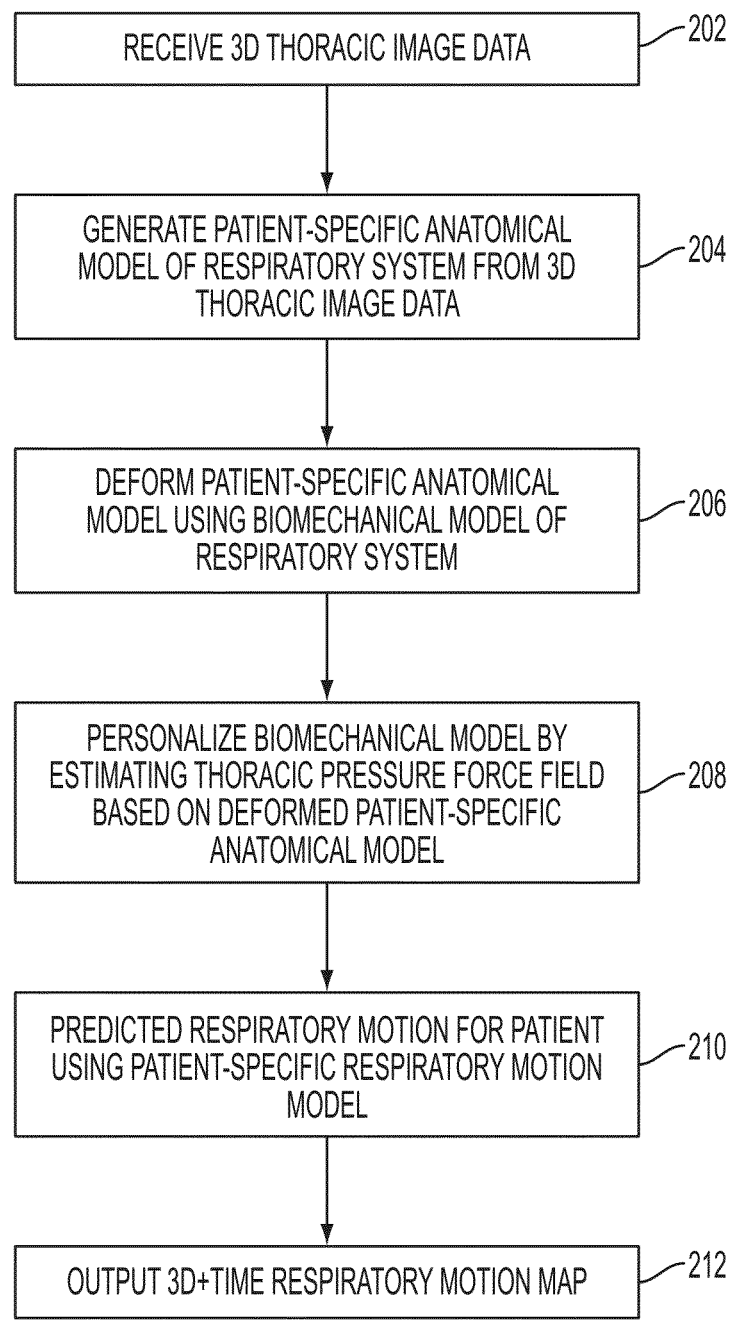
FIG. 2 illustrates a method of predicting respiratory motion of a patient according to an embodiment of the present invention.

FIG. 2 illustrates a method of predicting respiratory motion of a patient according to an embodiment of the present invention. The method of FIG. 2 transforms 3D or 4D thoracic medical images to generate a predicted 3D+time respiratory motion map. Referring to FIG. 2, at step 202, 3D thoracic image data is received. The 3D thoracic image data may include a single 3D thoracic image or multiple 3D thoracic images. The 3D thoracic image data may be a 4D thoracic image set, which is sequence of 3D medical images of at least the thorax of a patient over time. In advantageous implementations, the thoracic images may be CT or MR images, but the present invention is not limited thereto, and other imaging modalities may be used as well. The thoracic images may be received directly from an image acquisition device, such as a CT or MR scanner, or the thoracic images may be received by loading previously acquired images of a patient from a memory or storage of a computer system or another computer readable medium.

At step 204, a patient-specific anatomical model of the respiratory system is generated from the thoracic images. In order to represent the anatomy and allow physiologically correct motion, the detailed anatomical model of the respiratory system includes at least the lungs, thorax, and a sub-diaphragm region grouping abdominal organs including the diaphragm. This allows individual sliding of the lungs and the diaphragm along the thorax. The patient-specific anatomical model is generated from a single 3D thoracic image representing a single respiratory phase.

Figure 3:
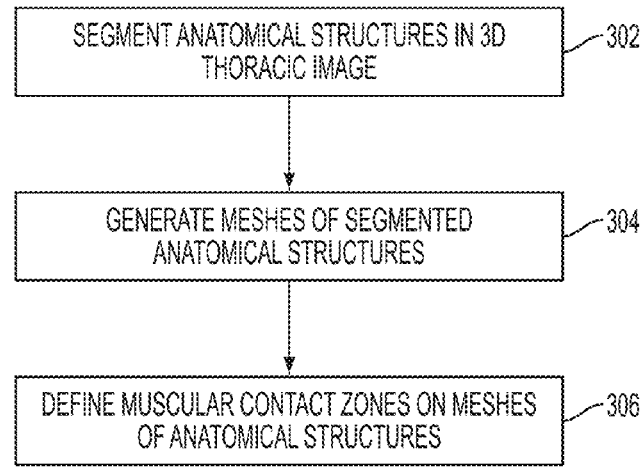
FIG. 3 illustrates a method of generating a patient-specific anatomical model of the respiratory system from a 3D image according to an embodiment of the present invention.

FIG. 3 illustrates a method of generating a patient-specific anatomical model of the respiratory system from a 3D image according to an embodiment of the present invention. The method of FIG. 3 can be used to implement step 204 of FIG. 2. Referring to FIG. 3, at step 302, anatomical structures are segmented in a 3D thoracic image. The 3D thoracic image may be a frame of a 4D thoracic image set, but the present invention is not limited thereto. In an advantageous implementation, the 3D image can be segmented using an automatic multi-organ segmentation technique based on a machine-learning approach with a level-set optimization, as described in United States Published Patent Application No. 2012/0230572, which is incorporated herein by reference in its entirety. While the lungs are directly segmented using this segmentation method, the thorax is segmented based on the skin and lung segmentations. In some patients, a strong diaphragm curvature and deep belly breathing causes an important sliding movement of the diaphragm along the rib cage, which can be observed in a 4D thoracic image set (e.g., CT or MRI). To allow this movement in the model, the diaphragm is segmented independently from the rib cage.

Figure 4:
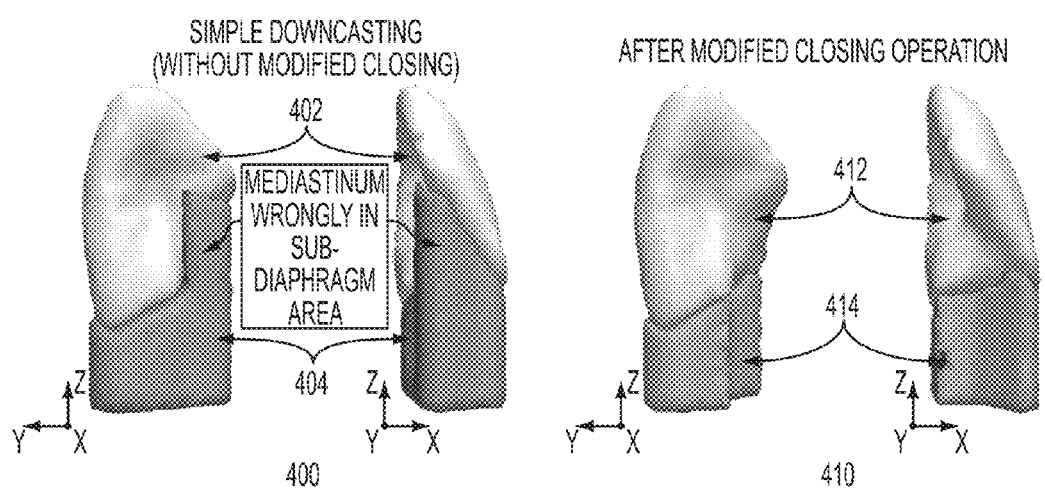
FIG. 4 illustrates segmentation of the sub-diaphragm region with and without a modified closing operation.

The sub-diaphragm is automatically determined by casting each detected lung downwards. However, due to the non-convex nature of the lung, a simple downward projection of the lung will cause outliers and sub-diaphragm wedges between the lung and the thorax. Therefore, a modified closing operation is performed on a height map generated from the segmented lung. In particular, a height map of the inferior surface (z-axis) of the lung is generated, and then the modified closing operation is applied. The modified closing operation is applied by performing erosion and dilation on voxels in the height map if greater than 60% (set experimentally) of the neighboring voxels have a lower value or if the value of the voxel is greater than 33% of the height of the lung. FIG. 4 illustrates segmentation of the sub-diaphragm region with and without the modified closing operation. As illustrated in FIG. 4, image 400 shows a segmented lung 402 and sub-diaphragm region 404 generated using simple downcasting without the modified closing operation. As shown in image 400, the mediastinum is wrongly included in the sub-diaphragm region 404. Image 410 shows the segmented lung 412 and sub-diaphragm region 414 after the modified closing operation is performed.

Figure 5:
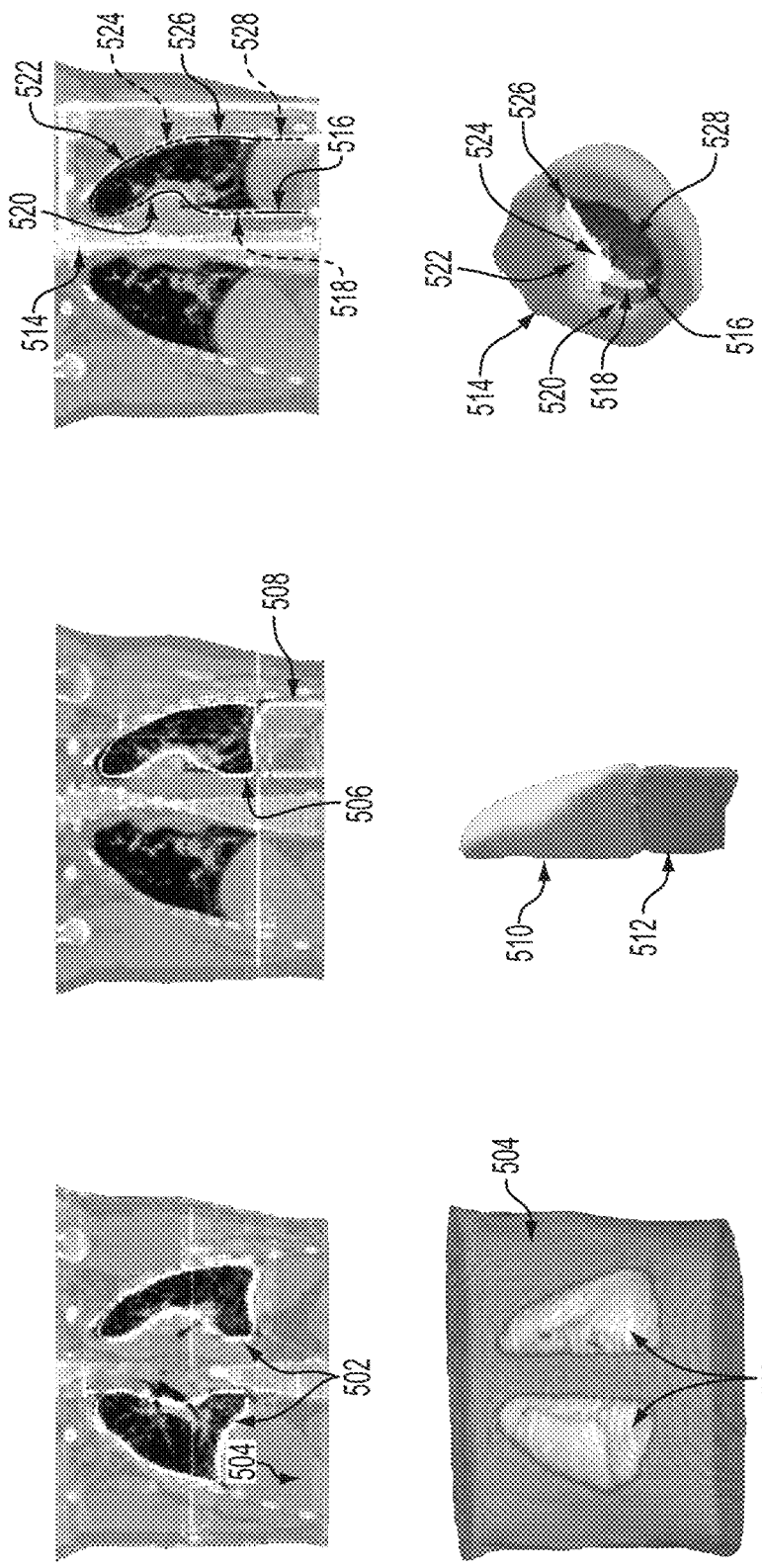
FIG. 5 illustrates exemplary results of the steps of the method of FIG. 3.

Returning to FIG. 3, at step 304, meshes are generated for the segmented anatomical structures. In particular, volumetric meshes (e.g., tetrahedral or hexahedral meshes) are generated for the segmented anatomical structures, resulting in a respective mesh for each of the lungs, sub-diaphragm region, and thorax. For example, the volumetric meshes can be generated using the Computational Geometry Algorithms Library (CGAL), but the present invention is not limited thereto, and any mesh generation algorithm can be used. FIG. 5 illustrates exemplary results of the steps of the method of FIG. 3. As illustrated in FIG. 5, column (a) shows exemplary segmentation results for the lungs 502 and thorax 504 segmented in a CT image. Column (b) shows exemplary segmentation results for a lung 506 and a sub-diaphragm region 508 in a CT image, as well as volumetric meshes 510 and 512 generated for the lung and sub-diaphragm region, respectively.

Returning to FIG. 3, at step 306, muscular contact zones are defined on the meshes of the segmented anatomical structures. In order to capture heterogeneous muscle forces, thoracic and diaphragmatic pressures are estimated regionally based on surface zones, henceforth called pressure zones. These pressure zones are defined automatically be sub-dividing the inner surface of the thorax by evenly spaced rings around the roughly cylinder-like thoracic cavity. Based on the relative angular position of each surface triangle, the rings are split into zones. In an advantageous implementation, the angle is defined to be 0° along the negative x-axis (dexter) and 90° along the negative y-axis (anterior). Furthermore, the superior surface of the sub-diaphragm (i.e., the diaphragm interface) is split into zones based on the relative position of each triangle on the anteroposterior (y) and destroy-sinister (x) axes. Column (c) of FIG. 5 illustrates muscular contact zones (pressure zones) 514, 516, 518, 520, 522, 524, 526, and 528 defined by sub-dividing the inner surface of the thorax into evenly spaced rings and splitting each of the rings into zones based on the angular positions the surface triangles of the mesh.

The method of FIG. 3 is used to generate the patient-specific anatomical model of the respiratory system from a 3D thoracic image. According to an advantageous embodiment of the present invention a first patient-specific anatomical model can be generated from a first 3D thoracic image at a first respiratory phase and a second patient-specific anatomical model can be generated from a second 3D thoracic image at a second respiratory phase. The first and second 3D thoracic images may be first and second frames of a 4D (3D+time) thoracic image sequence, but the present invention is not limited thereto. The first patient-specific anatomical model of the respiratory system at the first respiratory phase is deformed at step 206 and the second patient-specific anatomical model at the second respiratory phase is used as a basis for comparison for estimating the thoracic pressure force field at step 208. In an advantageous implementation, the first respiratory phase can be the end of exhale (EE) phase and the second respiratory phase can be the end of inhale (EI) phase, however the present invention is not limited thereto and any two distinct instants in the respiratory cycle can be used for the first and second respiratory phases. Several instants of the respiratory cycle could also be used for finer pressure estimation. In particular, the present invention is not limited to two thoracic images, but can be implemented with a larger number of thoracic images at different respiratory phases to better model pressure variation dynamics.

Returning to FIG. 2, at step 206, the patient-specific anatomical model of the respiratory system is deformed by a biomechanical model of the respiratory system that is driven by a thoracic pressure field. When first and second patient-specific anatomical models are generated at respective first and second respiratory phases in step 204, the first patient-specific anatomical model is deformed from the first respiratory phase to the second respiratory phase using the biomechanical model of the respiratory system. The biomechanical model uses the patient-specific anatomical model and simulated deformation under a set of pressure forces applied on the thoracic and diaphragm pressure zones. To solve the dynamics equations, the finite element method is applied, which incorporates mechanical parameters, the respiratory forces, and a specialized collision model.

Biomechanical Model:

The deformation of the lungs is computed by simultaneously solving the following dynamics equations for the lungs (l), thorax (t), and sub-diaphragm region (d):

$$\begin{cases} M^l \ddot{U}^l + C^l \dot{U}^l + K^l U^l = F_c^{t \to l} + F_c^{d \to l} \\ M^t \ddot{U}^t + C^t \dot{U}^t + K^t U^t = F_c^{l \to t} + F_c^{d \to t} + F_p^t \\ M^d \ddot{U}^d + C^d \dot{U}^d + K^d U^d = F_c^{l \to d} + F_c^{t \to d} + F_p^d \end{cases} \quad (1)$$

where the accelerations, velocities, and position of the free nodes of each part (lungs, thorax, and sub-diaphragm region) are gathered in the vectors $\ddot{U}$, $\dot{U}$, and $U$, respectively. It should be noted that the superscripts l, t, and d are omitted if not necessary for understanding. The lumped mass matrix M can be calculated for each part using predetermined mass density values. For example, the lumped mass matrix M can be calculated for the lungs using $\rho^l = 1.05$ g/mL and for the thorax and sub-diaphragm region using $\rho^{\{t,d\}} = 1.50$ g/mL. The stiffness matrix K describes the internal elastic forces. The damping matrix C represents the Rayleigh damping and can be implemented with coefficients of 0.1 for mass and stiffness. The right hand side of Equations (1) represents the forces of which the lungs, thorax, and sub-diaphragm region are subject to. The pressure forces $F_p$ represent the physiological forces driving the respiratory motion, while the interaction forces $F_c$ model the sliding interaction between the organs. An implicit Euler scheme can be used to integrate Equation (1) in time, since such a scheme allows larger time steps.

Tissue Model:

According to an exemplary embodiment, non-linear, heterogeneous material properties of the lung, thorax, and muscles are simplified and represented in a linear elastic model. A co-rotational formula is used to cope with large deformations. The Young's modulus Y and the Poisson's ratio v define the mechanical properties, especially the stiffness and compressibility, respectively. In a possible implementation, the sub-diaphragm and thorax tissue can be assumed to be $Y^{\{t,d\}}$=7800 kPa, while the lungs are softer with $Y^l$=900 kPa. In a possible implementation, the thorax and sub-diaphragm region are more incompressible ($v^{\{t,d\}}$=0.43) than the lungs ($v^l$=0.4). It is to be understood that the present invention is not limited to these particular values and other values may be used as well. Similarly, other material models may be used as well. Furthermore, it is also possible that patient-specific values for these tissue properties can be estimated in addition to the patient-specific thoracic pressure force field. Young's modulus Y and the Poisson's ratio v for each part define the stiffness matrix K for that part.

Respiratory Pressure Forces:

The lungs are moved passively by the surrounding muscles. According to an advantageous embodiment of the present invention, the biomechanical model of the respiratory system represents this behavior by applying pressures on the automatically pre-defined thoracic and diaphragm pressure zones, which are translated through the collision and sliding interaction model to the lung as described below. For every zone $z^i$, the pressure $p^i$ is applied as a force $f_p^i = p^i n dS$, where n is the normal of the surface element dS.

Collision and Sliding Interaction:

According to an advantageous embodiment of the present invention, a specialized collision model is used to reflect pleura behavior. The collision model aims to keep the lung attached to diaphragm and thoracic cavity without inter-penetration. To that end, the distance d between the meshes is kept at an optimal distance $d_o$, while applying a strong force when d falls below a minimal contact distance $d_c$, a continuously decreasing force when d converges towards $d_o$, and no force when the distance between the meshes is greater than an alarm distance $d_a$. The optimal distance $d_o$ can be expressed as:

$$d_o = d_c + \frac{d_a - d_c}{2}. \qquad (2)$$

Figure 6:
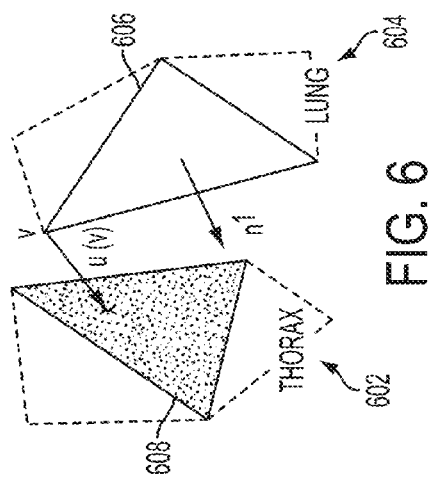
FIG. 6 illustrates vectors for computing the collision and sliding interaction between the thorax mesh and the lung mesh.

In an exemplary implementation, the distances have been empirically set to $d_c$=1 mm and $d_a$=5 mm. Once a collision between two meshes is detected ($d_c \leq d \leq d_a$), the contact force $F_c^{m_1 \to m_2}$ is applied from mesh $m_1$ to mesh $m_2$:

$$\begin{cases} F_c^{m_1 \to m_2}(v) = 0, & \text{if } d < 0 \text{ or } d > d_a \\ F_c^{m_1 \to m_2}(v) = -n^{m_2} k_s(u(v) \cdot n^{m_2}), & \text{if } 0 \leq d \leq d_a, \end{cases} \qquad (3)$$

where u is the vector between the vertex v, which belongs to the triangle $\mathcal{T}^{m_2}$ on mesh $m_2$, and the corresponding collision point on mesh $m_1$, and is used to calculate the current distance $d=\|u(v)\|$. Furthermore, $n^{m_2}$ is the normal of the triangle $\mathcal{T}^{m_2}$ and $k_s$ is a penalty force stiffness coefficient, which can be set to 0.1 N/m in an exemplary implementation. The interactions $F_c$ between all three meshes (lungs, thorax, and sub-diaphragm region) are defined in a similar way, as described above. FIG. 6 illustrates vectors for computing the collision and sliding interaction between the thorax mesh and the lung mesh. As shown in FIG. 6, the thorax mesh 602 collides with the lung mesh 604. u(v) is the vector between the vertex v, which belongs to triangle 606 on the lung mesh 604, and the corresponding collision point 608 on the thorax mesh 602. $n^l$ is the normal of triangle 606. The contact force applied from the thorax mesh 602 to the lung mesh 604 is calculated as described above in Equation (3).

Stopping Criteria:

When forces are applied, the biomechanical model converges toward a stable state where the dynamics equations (Equation (1)) are balanced. Unfortunately, solving these equations numerically may result in a converged state with very small oscillations. According to an advantageous implementation, a stopping criteria is defined to determine when the simulation reaches a state which is numerically converged. A first criteria is met when a user-defined maximum simulation time (e.g., $T_{max}$=1 sec) is reached. It may happen in that case that the simulation has not converged. Yet, the results may still be accepted because they still give the optimizer a hint about the behavior of the model. $T_{max}$ can be set experimentally under the consideration that the simulation time may not directly correlate to the real breathing time. The second and third criteria are based on velocities, which are calculated at every time step i. The second criteria is met when the simulation becomes unstable. In particular, if the velocity of any node in the lung becomes physiologically impossible (e.g., greater than $1 \times 10^3$ m/s), the simulation is aborted. The third criteria is met when the sliding average of the mean velocity of all nodes in the lung fall below a given threshold, e.g., $\epsilon = 2.5 \times 10^{-4}$ m/s (set experimentally), which represents the numerical instability of the solution of Equation (1). In order to reduce the influence of noise on the evaluation of the stopping criteria, the moving average $\bar{v}(i)$ is calculated over the last n samples. For example, n=50 has been shown to overcome fluctuations due to noise. The values in the sliding window are initialized with zeros and the test is enabled after i>n. According to various implementations, the simulation may be performed with any one of the above described stopping criteria individually, any combination of the above described stopping criteria, or all of the above described stopping criteria.

Returning to FIG. 2, at step 208, the biomechanical model of the respiratory system is personalized by estimating the thoracic pressure field based on the deformed patient-specific anatomical model, resulting in a patient-specific respiratory motion model. In particular, a patient-specific thoracic pressure field is calculated by estimating the pressure necessary to load the lungs in the patient-specific anatomical model from a first respiratory phase (e.g., EE) to a second respiratory phase (e.g., EI). According to an advantageous embodiment, the pressure necessary to load the lungs from EE to EI is estimated by minimizing a multi-variate cost function using Powell's NEWUOA algorithm, a trust-region method that does not explicitly calculate cost function gradients. Three different cost functions can be defined as:

$$c_1 = d_S, c_2 = d_{LM}, \text{ and } c_3 = d_S + d_{LM} \qquad (4)$$

where $d_S$ is the mean Hausdorff surface-to-surface distance between the deformed EE lung surface (first patient-specific anatomical model deformed by the biomechanical model) and the segmented lung surface at EI (second patient-specific anatomical model), and $d_{LM}$ is the average Euclidean distance between internal landmarks at EI and their corresponding EE landmarks moved according to the internal deformation provided by the biomechanical model. Any one of the cost functions, or a combination of the cost functions, can be used as a basis for personalizing the motion model by estimating the patient-specific thoracic pressure force field. The optimizer (e.g., the NEWUOA algorithm) calculates a thoracic pressure force field to minimize the cost function. According to an advantageous embodiment of the present invention, in order to reduce convergence problems and minimize risks of local minima of the optimization algorithm with many parameters, a coarse-to-fine strategy can be implemented as follows: (1) Start the optimizer with one pressure zone on the sub-diaphragm and the thorax and set the initial pressure values to zero. (2) Restart the optimizer with more zones and set the initial pressures with the optimal values of the previous result. The thorax zones are horizontally split in two equal parts and each part is vertically split into two equal parts. The sub-diaphragm zones are vertically split into two equal parts. (3) Repeat step (2) until a target number of pressure zones are reached. According to a possible implementation, once the patient-specific pressure force field is estimated, the estimated pressure force field can be displayed, for example on a display device of a computer system, for diagnostic purposes.

At step 210, respiratory motion of the patient is predicted using the patient-specific respiratory motion model. Once the patient-specific pressure force field is estimated in step 208, the patient-specific respiratory motion model, including the anatomical model, the biomechanical model, and the estimated pressure field, is generative and can be used to predict the respiratory motion of the patient. The respiratory motion of the patient is predicted by modulating the patient-specific thoracic pressure force field. The thoracic pressure force field can be modulated manually or in correlation with a surrogate signal. In response to the pressure force field being modulated, the biomechanical model is driven by the pressure force field and the deformation of the patient-specific anatomical model of the respiratory system over a period of time is simulated, resulting in a 3D+time map of the respiratory motion. In a possible implementation, the simulation of inhale is driven by the personalized pressure values and the simulation of the exhale is achieved by setting the pressure values equal to zero.

At step 212, a 3D+time respiratory motion map is output. The 3D+time respiratory motion map can be output by displaying the 3D+time respiratory motion map on a display device of a computer system. The 3D+time respiratory motion map can also be output by storing the 3D+time respiratory motion map on a memory or storage of a computer system.

Figure 7:
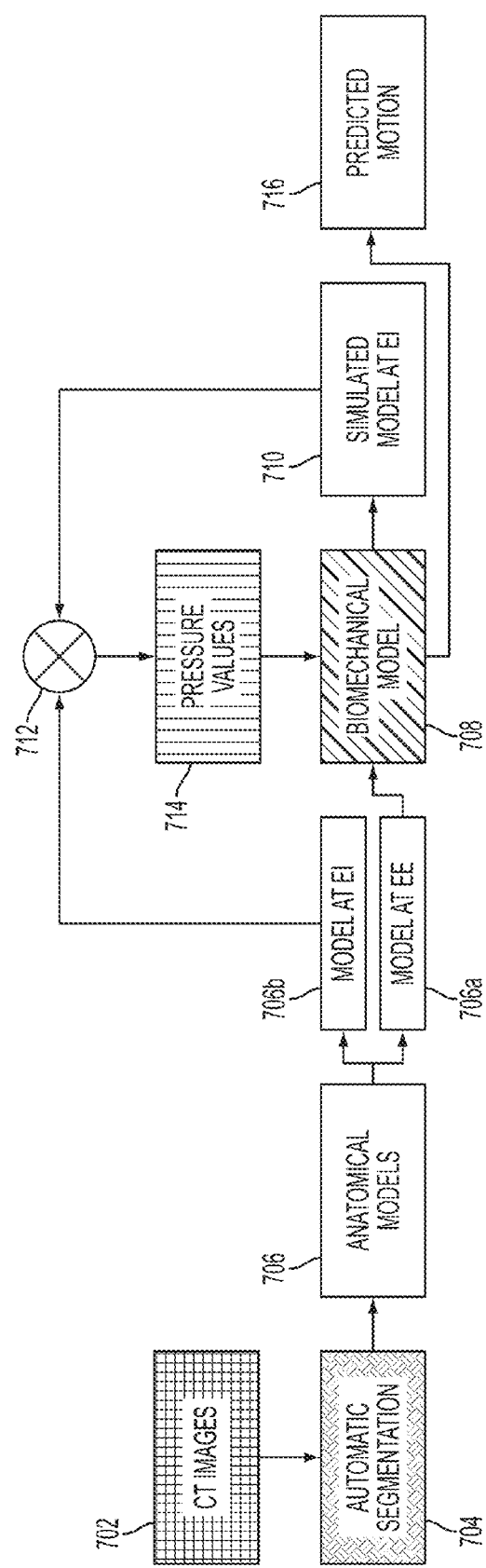
FIG. 7 illustrates a pipeline for an exemplary implementation of the method of FIG. 2 according to an embodiment of the present invention.

FIG. 7 illustrates a pipeline for an exemplary implementation of the method of FIG. 2 according to an embodiment of the present invention. As illustrated in FIG. 7, CT images 702 of the thoracic region of a patient are received. At 704, the CT images 702 are automatically segmented resulting in patient-specific anatomical models 706, including a patient-specific anatomical model at the EE respiratory phase 706a and a patient-specific anatomical model at the EI respiratory phase 706b. The biomechanical model 708 is used to deform the first patient-specific anatomical model 706a, resulting in a simulated model at EI 710. At 712, the simulated model at EI 710 is compared to the second patient-specific anatomical model 706b, and pressure values 714 are estimated to minimize a cost function. Once the patient-specific pressure values 714 are estimated, the pressure values 714 are modulated to drive the biomechanical model 708 in order to predict the respiratory motion, and the predicted respiratory motion 716 is output, for example in the form of a 3D+time respiratory motion map.

The predicted respiratory motion of the patient can be used for motion compensation for improved image reconstruction or therapy guidance. According to a possible embodiment, a respiratory gated signal (e.g., CT or PET) can be acquired and reconstruction can be performed for each (binned) respiratory phase. The gating can be done using an external device (e.g., belt, 3D camera, etc.) or using real-time imaging (surrogate free). Internal organs can be estimated in the gated signal and the biomechanical model can be fit as described above in the method of FIG. 2 so that the model matches the data as much as possible. Various surrogates can be indicated based on the estimated motion model (e.g., skin, tumor, specific anatomy) and re-binning and reconstruction can be performed based on the revised surrogate derived from the regulated matched 4D biomechanical model. Such motion compensation can be performed for two or more imaging modalities acquired subsequent to one another (e.g., molecular/anatomical imaging). According to another possible embodiment, the motion compensation can be used to devise a spatially dependent blurring filter and its inverse to remove a motion blur effect from the aggregated reconstruction. Aggregated reconstruction is the reconstruction where all the acquired data is used for 3D reconstruction without binning (gating).

The present inventors evaluated the above described methods for respiratory motion prediction using 4D CT data sets where the entire thorax is visible and landmarks are available. The segmentation of the lungs and skin was performed automatically and a pre-processing pipeline automatically detected the lungs, thorax, and sub-diaphragm regions. Convergence analyses for spatial resolution, temporal resolution, and the number of pressure zones were performed using the cost function $c_3$ and if not otherwise specified, with 4 pressure zones on the diaphragm and 16 pressure zones along the thoracic cavity.

Four different mesh configurations were generated with 789, 1393, 2603, and 5692 tetrahedra elements for the lung, while the number of elements in the thorax and sub-diaphragm were left constant at 6813 and 902, respectively. The accuracy of the interpolation landmark position is directly proportional to the number of tetrahedral elements. However, the number of tetrahedral elements also affects collision accuracy and computation time. Table 1 shows mean errors between simulated results and ground truth for the different spatial resolutions of the lung mesh. Based on the error data of Table 1, the 2.6 k configuration can be used in an advantageous implementation, as the 5.6 k setup has a longer computation time while not yielding significantly improved errors.

TABLE 1

| | Number of Tetrahedra Elements | | | |
|---|---|---|---|---|
| | 0.7k | 1.3k | 2.6k | 5.6k |
| EI surface error (mm) | 2.81 | 2.19 | 2.18 | 2.00 |
| EI landmark error (mm) | 3.50 | 3.40 | 3.52 | 3.52 |
| Standard deviation (mm) | 1.92 | 1.85 | 1.97 | 1.95 |
| 90%-tile landmark error (mm) | 6.93 | 5.06 | 5.57 | 5.74 |
| Average computation time (s) | 122 | 132 | 184 | 281 |

Figure 8:
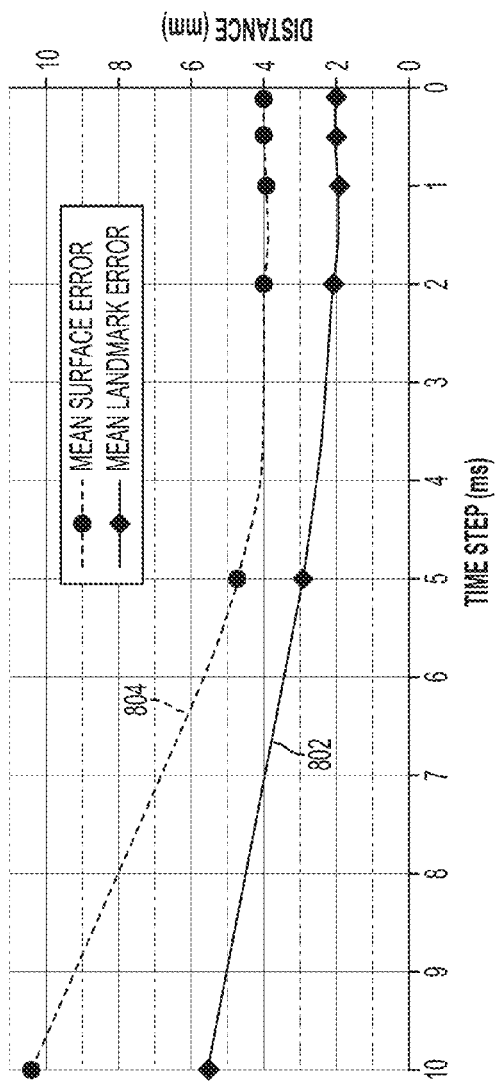
FIG. 8 illustrates mean errors between the simulation and ground truth for different temporal resolutions.

FIG. 8 illustrates mean errors between the simulation and ground truth for different temporal resolutions. In particular, FIG. 8 shows the mean surface error 802 and the mean landmark error 804 with simulations performed using different time steps. According to an advantageous implementation, the default time step of the simulation can be set to 1 ms. As shown in FIG. 8, time steps smaller than 1 ms do not change the result, while larger time steps significantly worsen the results, mainly because of poor collisions. Accordingly, a time step of 1 ms provides a compromise between accuracy and computation time.

Figure 9:
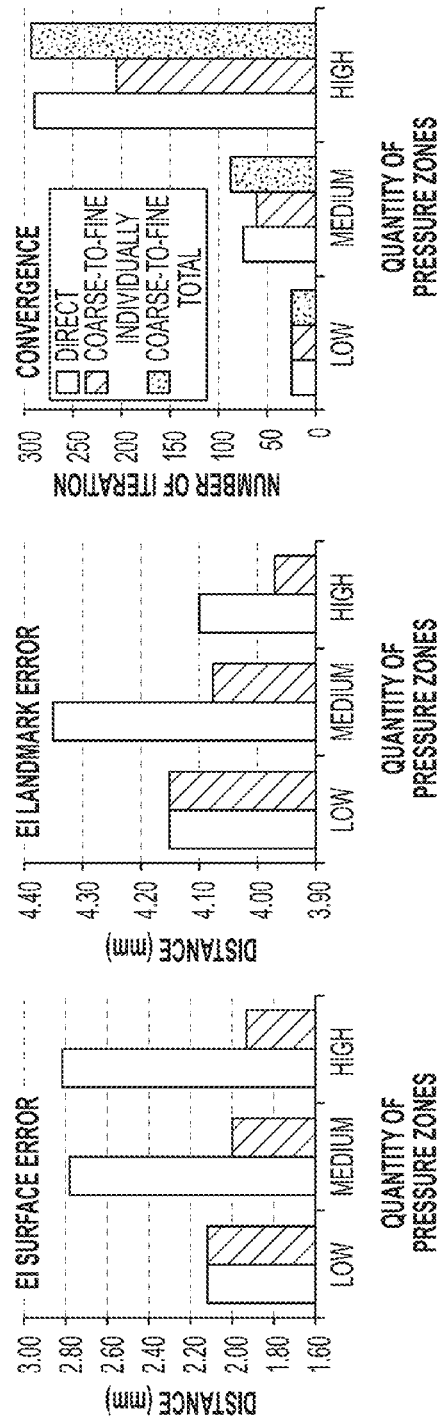
FIG. 9 illustrates a comparison between a direct optimization strategy and a coarse-to-fine optimization strategy with different numbers of pressure zones.
Figure 10:
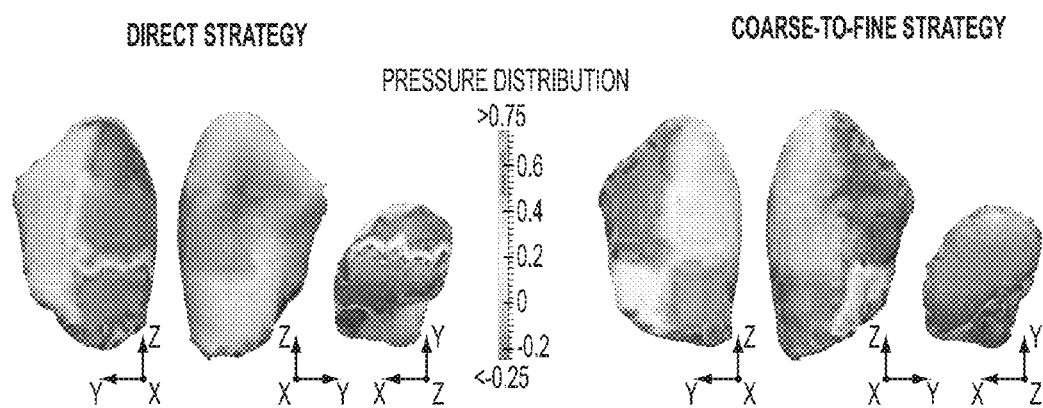
FIG. 10 illustrates pressure distributions resulting from the direct optimization strategy and the coarse-to-fine optimization strategy.

The number of pressure zones and the optimization strategy for estimating the pressure values influence the prediction and the generation of a physiological plausible smooth pressure distribution. FIG. 9 illustrates a comparison between a direct optimization strategy and a coarse-to-fine optimization strategy with different numbers of pressure zones. Three configurations of pressure zones are used: (1) Low: one zone on the sub-diaphragm and one zone on the thorax; (2) Medium: two zones on the sub-diaphragm and two rings with two zones per ring on the thorax; and (3) High: four zones on the sub-diaphragm and four rings with four zones per ring on the thorax. The coarse-to-fine strategy for the medium configuration uses the result of the low optimization. The coarse-to-fine strategy for the high configuration uses the result of the medium optimization. As shown in FIG. 9, stability and more accurate solutions are gained when there are four zones on the diaphragm and 16 zones on the thoracic surface. The NEWUOA algorithm converges faster and the sum of the total number of iterations of the low, medium, and high optimization for the coarse-to-fine strategy (295) is on the same order of magnitude of the number of iterations of the direct high optimization (292), but achieves more robust and accurate solutions. FIG. 10 illustrates pressure distributions resulting from the direct optimization strategy and the coarse-to-fine optimization strategy. As shown in FIG. 10, the pressure distribution resulting from the direct optimization strategy is discontinuous, whereas the pressure distribution resulting from the coarse-to-fine strategy is smooth. According to an advantageous implementation, 4 and 16 pressure zones can be used on the sub-diaphragm and thorax, respectively, and the pressure force field can be estimated with the coarse-to-fine optimization strategy.

Figure 11:
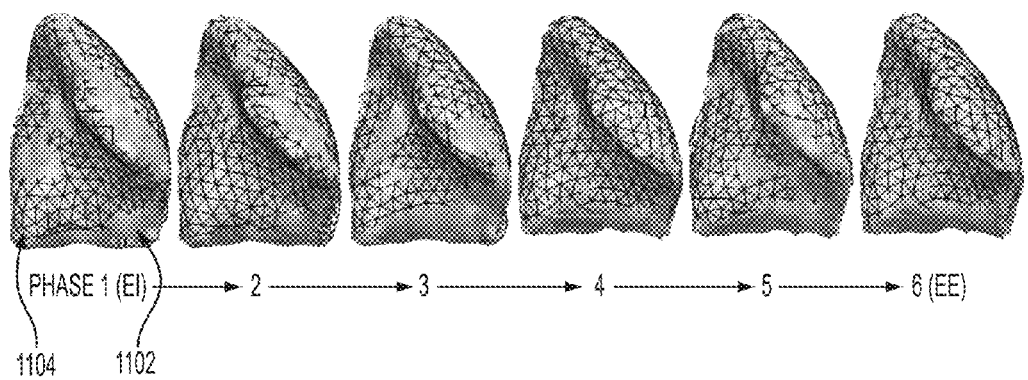
FIG. 11 illustrates the simulated respiratory motion of the lung from the end-inhale (EI) respiratory phase to the end-exhale (EE) respiratory phase.
Figure 12:
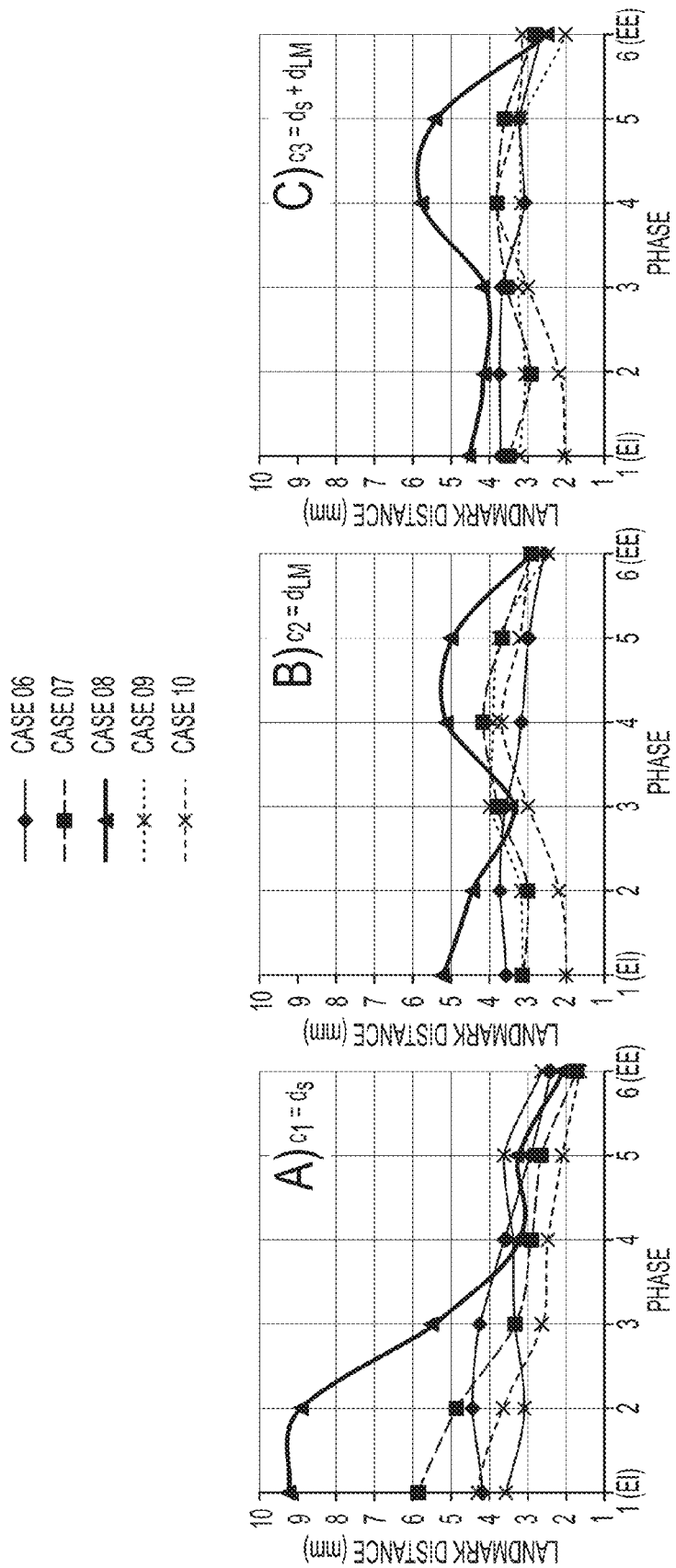
FIG. 12 illustrates the average landmark error during exhale for three cost functions.

Using the patient data, the meshing resulted in an average over all patients of 3388, 18648, and 2326 for the lung, thorax, and sub-diaphragm, respectively. Results for the left lung only are described herein, but due to anatomical separation, the method can easily be extended to both lungs. Simulations were performed for each cost function described above in Equation (4) in order to assess the influence of the cost functions on the personalization. The personalization automatically estimates pressure values for each muscular contact zone, which enables the deformation of the lung from EE to EI. Depending on the number of pressure zones, the optimization algorithm converges after an average of 24, 55, 198, and 277 iterations for low, medium, and high number of zones, and coarse-to-fine strategy, respectively. Each iteration runs a full simulation of lung motion based on a set of pressure values, where the average computation time was 2 min. The quality of each personalization was the evaluated by predicting the exhale (EI to EE) without any image information. A full cycle was simulated to evaluate the quality of the prediction based on the three cost functions. The simulation of inhale was driven by the personalized pressure values, while exhale is simulated by setting the pressure values to zero. The surface and landmark errors were calculated at EI and for all corresponding phases during exhale, where synchronization is performed by means of the lung volume and therefore represents a real-world scenario. The quality of the exhale prediction was evaluated by comparing landmarks for every intermediate phase. FIG. 11 shows the simulated respiratory motion of the lung from the EI respiratory phase to the EE respiratory phase. In particular, FIG. 11 shows the simulated lung 1102 (solid) and the ground truth 1104 (wire frame) acquired from 4D CT data for each phase between EI and EE. Table 2 shows errors between simulations and ground truth for the personalization and the exhale prediction using the different cost functions. FIG. 12 illustrates the average landmark error during exhale for the three cost functions. As shown in Table 2 and FIG. 12, the model based on cost function $c_3$ performed best and a mean landmark error over all landmarks and phases during exhale of 3.40±1.0 mm was obtained.

TABLE 2

| Case | 6 | 7 | 8 | 9 | 10 | Mean |
|---|---|---|---|---|---|---|
| Experiment 1: $c_1 = d_S$ | | | | | | |
| EI surface error (mm) | 1.75 | 2.03 | 2.09 | 2.16 | 1.36 | 1.88 ± 0.52 |
| EI landmark error (mm) | 4.20 | 5.84 | 9.24 | 3.58 | 4.36 | 5.44 ± 3.80 |
| Mean landmark error during prediction (mm) | 3.63 | 3.55 | 5.35 | 3.27 | 2.82 | 3.72 ± 1.63 |
| Experiment 2: $c_2 = d_{LM}$ | | | | | | |
| EI surface error (mm) | 2.35 | 3.46 | 2.93 | 2.44 | 2.32 | 2.70 ± 0.76 |
| EI landmark error (mm) | 3.55 | 3.13 | 5.17 | 3.14 | 1.95 | 3.38 ± 1.78 |
| Mean landmark error during prediction (mm) | 3.27 | 3.43 | 4.33 | 3.40 | 2.83 | 3.45 ± 0.88 |
| Experiment 3: $c_3 = d_g + d_{LM}$ | | | | | | |
| EI surface error (mm) | 2.09 | 2.78 | 3.28 | 2.21 | 2.05 | 2.48 ± 0.80 |
| EI landmark error (mm) | 3.67 | 3.49 | 4.53 | 3.23 | 2.03 | 3.39 ± 1.36 |
| Mean landmark error during prediction (mm) | 3.34 | 3.38 | 4.40 | 2.97 | 2.91 | 3.40 ± 1.00 |

As described above, the pressure force field is estimated using patient-specific anatomical models estimated at two different respiratory phases (EE and EI). According to an alternative embodiment, the pressure force field can also be estimated using the entire 4D sequence, yielding a non-linear pressure variation. In this embodiment, the cost function would then be evaluated over the entire sequence instead of at one time frame.

According to a possible embodiment, the patient-specific pressure force field can be correlated to external surrogates for lung motion prediction and image reconstruction. Using a database of pairs (patient-specific pressures/surrogate signal), a regression model can be learned using statistical learning techniques. For a new patient, the regression model can then be used to predict the pressure force field. A pre-calibration step based on the estimation process described above could be employed for better accuracy.

Embodiments of the present invention can be applied to any organ that deforms due to respiratory motion. The framework described herein can cope with multiple objects.

Although described above as utilizing linear tissue properties for the organs, the present invention is not limited thereto and non-linear tissue properties can be used as well. According to a possible embodiment, the tissue properties can be estimated along with the pressure force field in order to further personalize the biomechanical model. In this case the tissue properties are adjusted along with the pressure values to minimize the cost function.

According to a possible embodiment, airways can be used to further constrain the respiratory motion and make it more realistic. For example, the airways can be segmented in CT images and the segmented airways can be modeled as linear springs.

According to a possible embodiment, the personalization procedure could be achieved using machine-learning techniques. The forward model of respiratory motion can be employed to generate a large database of observations (pairs of pressure force field and lung motion). A regression model can then be estimated between the lung motion and the model parameters using non-linear manifold learning. The personalization of new datasets can then involve only the evaluation of the regression model.

Figure 13:
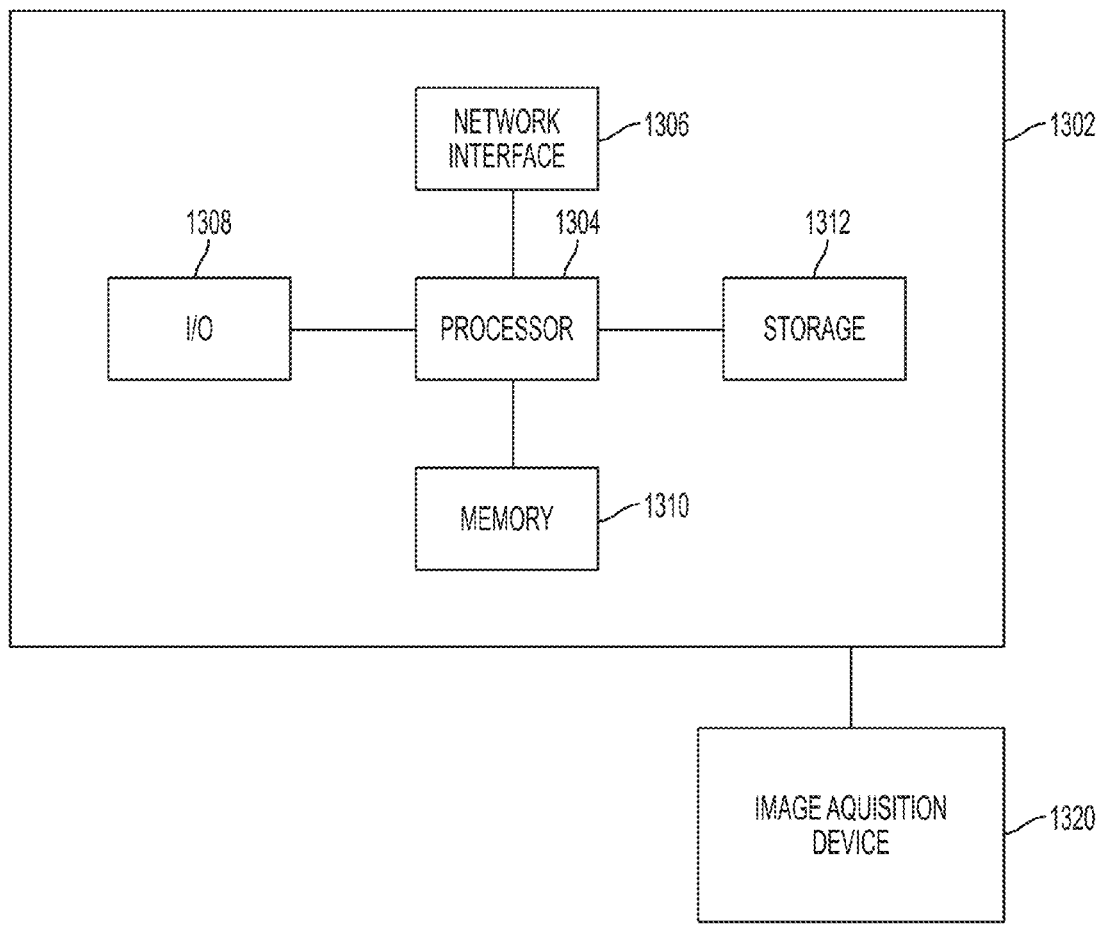
FIG. 13 is a high-level block diagram of a computer capable of implementing the present invention.

The above-described methods for prediction of respiratory motion from 3D thoracic images can be implemented on a computer using well-known computer processors, memory units, storage devices, computer software, and other components. A high-level block diagram of such a computer is illustrated in FIG. 13. Computer 1302 contains a processor 1304, which controls the overall operation of the computer 1302 by executing computer program instructions which define such operation. The computer program instructions may be stored in a storage device 1312 (e.g., magnetic disk) and loaded into memory 1310 when execution of the computer program instructions is desired. Thus, the steps of the methods of FIGS. 2, 3, and 7 may be defined by the computer program instructions stored in the memory 1310 and/or storage 1312 and controlled by the processor 1304 executing the computer program instructions. An image acquisition device 1320, such as a CT scanning device, C-arm image acquisition device, MR scanning device, Ultrasound device, etc., can be connected to the computer 1302 to input image data to the computer 1302. It is possible to implement the image acquisition device 1320 and the computer 1302 as one device. It is also possible that the image acquisition device 1320 and the computer 1302 communicate wirelessly through a network. The computer 1302 also includes one or more network interfaces 1306 for communicating with other devices via a network. The computer 1302 also includes other input/output devices 1308 that enable user interaction with the computer 1302 (e.g., display, keyboard, mouse, speakers, buttons, etc.). Such input/output devices 1308 may be used in conjunction with a set of computer programs as an annotation tool to annotate volumes received from the image acquisition device 1320. One skilled in the art will recognize that an implementation of an actual computer could contain other components as well, and that FIG. 13 is a high level representation of some of the components of such a computer for illustrative purposes.

The foregoing Detailed Description is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that various modifications may be implemented by those skilled in the art without departing from the scope and spirit of the invention. Those skilled in the art could implement various other feature combinations without departing from the scope and spirit of the invention.

The invention claimed is:

1. A method for predicting respiratory motion of a patient, comprising:
   generating a patient-specific anatomical model of the respiratory system from a 3D thoracic image of the patient;
   deforming the patient-specific anatomical model of the respiratory system using a biomechanical model;
   personalizing the biomechanical model for the patient by estimating a patient-specific thoracic pressure force field to drive the biomechanical model; and
   predicting respiratory motion of the patient using the personalized biomechanical model driven by the patient-specific thoracic pressure force field,
   wherein the patient-specific anatomical model includes at least one lung region, a thorax region, and a sub-diaphragm region, and generating the patient-specific anatomical model of the respiratory system from the 3D thoracic image of the patient comprises:
      segmenting the at least one lung region, the thorax region, and the sub-diaphragm region in the 3D thoracic image;
      generating a respective mesh for each of the segmented at least one lung region, thorax region, and sub-diaphragm region; and
      defining a plurality of pressure zones on the meshes for the thorax region and the sub-diaphragm region.

2. The method of claim 1, further comprising:
   displaying a 3D+time respiratory motion map showing the predicted respiratory motion.

3. The method of claim 2, further comprising:
   performing one of image reconstruction or therapy delivery using the 3D+time respiratory motion map.

4. The method of claim 1, wherein defining a plurality of pressure zones on the meshes for the thorax region and the sub-diaphragm region comprises:
   defining pressure zones for the mesh of the thorax region by sub-dividing an inner surface of the thorax into a plurality of evenly spaced rings and splitting each ring into a plurality of pressure zones; and
   defining pressure zones for the mesh of the sub-diaphragm region by splitting a superior surface of the sub-diaphragm region into a plurality of zones.

5. The method of claim 1, wherein deforming the patient-specific anatomical model of the respiratory system using a biomechanical model comprises:
   deforming the meshes for the at least one lung region, thorax region, and sub-diaphragm region based on forces due to pressures applied to the plurality of pressure zones on the thorax mesh and the sub-diaphragm mesh and based on interaction forces between the thorax mesh, the sub-diaphragm mesh and the at least one lung mesh calculated using a collision model that models sliding interactions between the meshes.

6. The method of claim 5, wherein personalizing the biomechanical model for the patient by estimating a patient-specific thoracic pressure force field to drive the biomechanical model comprises:
   estimating pressures applied to the pressure zones of the thorax mesh and the sub-diaphragm mesh to deform the lung mesh from two images corresponding to a first respiratory phase and a second respiratory phase.

7. The method of claim 6, wherein estimating pressures applied to the pressure zones of the thorax mesh and the sub-diaphragm mesh to deform the lung mesh from two images corresponding to a first respiratory phase and a second respiratory phase comprises:

(a) performing an optimization algorithm to estimate optimal pressures applied to a single pressure zone on the thorax mesh and a single pressure zone one the sub-diaphragm mesh with predetermined initial values of the pressures;

(b) increasing a number of pressure zones on the thorax mesh and a number of pressure zones on the sub-diaphragm mesh;

(c) performing the optimization algorithm to estimate optimal pressures applied to the increased number of pressure zones on the thorax mesh and the sub-diaphragm mesh using previously estimated optimal pressure values as initial values; and (d) repeating steps (b) and (c) until a target number of pressure zones on the thorax mesh and sub-diaphragm mesh is reached.

8. The method of claim 1, wherein generating a patient-specific anatomical model of the respiratory system from a 3D thoracic image of the patient comprises:

generating a first patient-specific anatomical model from a first 3D thoracic image at a first respiratory phase; and generating a second patient-specific anatomical model from a second 3D thoracic images at a second respiratory phase.

9. The method of claim 8, wherein deforming the patient-specific anatomical model of the respiratory system using a biomechanical model comprises:

deforming the first patient-specific anatomical model from the first respiratory phase to the second respiratory phase using the biomechanical model.

10. The method of claim 9, wherein personalizing the biomechanical model for the patient by estimating a patient-specific thoracic pressure force field to drive the biomechanical model comprises:

comparing the deformed first patient-specific anatomical model with the second patient-specific anatomical model; and estimating a thoracic pressure force field that minimizes a cost function based on the comparison of the deformed first patient-specific anatomical model with the second patient-specific anatomical model.

11. The method of claim 10, wherein the first respiratory phase is an end-exhale (EE) phase and the second respiratory phase is an end-inhale (EI) phase.

12. The method of claim 1, wherein predicting respiratory motion of the patient using the personalized biomechanical model driven by the patient-specific thoracic pressure force field comprises:

modulating the patient-specific thoracic pressure force field; and deforming the patient-specific anatomical model using the personalized biomechanical model driven by the modulated patient-specific thoracic pressure force field.

13. The method of claim 1, wherein personalizing the biomechanical model for the patient by estimating a patient-specific thoracic pressure force field to drive the biomechanical model comprises:

estimating the patient-specific pressure force field to drive the model from a plurality of images corresponding to a plurality of respiratory phases.

14. An apparatus for predicting respiratory motion of a patient, comprising:

means for generating a patient-specific anatomical model of the respiratory system from a 3D thoracic image of the patient;

means for deforming the patient-specific anatomical model of the respiratory system using a biomechanical model;

personalizing the biomechanical model for the patient by estimating a patient-specific thoracic pressure force field to drive the biomechanical model; and means for predicting respiratory motion of the patient using the personalized biomechanical model driven by the patient-specific thoracic pressure force field, wherein the patient-specific anatomical model includes at least one lung region, a thorax region, and a sub-diaphragm region, and the means for generating a patient-specific anatomical model of the respiratory system from a 3D thoracic image of the patient comprises:

means for segmenting the at least one lung region, the thorax region, and the sub-diaphragm region in the 3D thoracic image;

means for generating a respective mesh for each of the segmented at least one lung region, thorax region, and sub-diaphragm region; and means for defining a plurality of pressure zones on the meshes for the thorax region and the sub-diaphragm region.

15. The apparatus of claim 14, further comprising:

means for displaying a 3D+time respiratory motion map showing the predicted respiratory motion.

16. The apparatus of claim 15, further comprising:

means for performing one of image reconstruction or therapy delivery using the 3D+time respiratory motion map.

17. The apparatus of claim 14, wherein the means for deforming the patient-specific anatomical model of the respiratory system using a biomechanical model comprises:

means for deforming the meshes for the at least one lung region, thorax region, and sub-diaphragm region based on forces due to pressures applied to the plurality of pressure zones on the thorax mesh and the sub-diaphragm mesh and based on interaction forces between the thorax mesh, the sub-diaphragm mesh and the at least one lung mesh calculated using a collision model that models sliding interactions between the meshes.

18. The apparatus of claim 17, wherein the means for personalizing the biomechanical model for the patient by estimating a patient-specific thoracic pressure force field to drive the biomechanical model comprises:

means for estimating pressures applied to the pressure zones of the thorax mesh and the sub-diaphragm mesh to deform the lung mesh from two images corresponding to a first respiratory phase and a second respiratory phase.

19. The apparatus of claim 14, wherein the means for generating a patient-specific anatomical model of the respiratory system from a 3D thoracic image of the patient comprises:

means for generating a first patient-specific anatomical model from a first 3D thoracic image at a first respiratory phase; and means for generating a second patient-specific anatomical model from a second 3D thoracic images at a second respiratory phase.

20. The apparatus of claim 19, wherein the means for deforming the patient-specific anatomical model of the respiratory system using a biomechanical model comprises:

means for deforming the first patient-specific anatomical model from the first respiratory phase to the second respiratory phase using the biomechanical model.

21. The apparatus of claim 20, wherein the means for personalizing the biomechanical model for the patient by estimating a patient-specific thoracic pressure force field to drive the biomechanical model comprises:
- means for comparing the deformed first patient-specific anatomical model with the second patient-specific anatomical model; and
- means for estimating a thoracic pressure force field that minimizes a cost function based on the comparison of the deformed first patient-specific anatomical model with the second patient-specific anatomical model.

22. The apparatus of claim 21, wherein the first respiratory phase is an end-exhale (EE) phase and the second respiratory phase is an end-inhale (EI) phase.

23. The apparatus of claim 14, wherein the means for predicting respiratory motion of the patient using the personalized biomechanical model driven by the patient-specific thoracic pressure force field comprises:
- means for modulating the patient-specific thoracic pressure force field; and
- means for deforming the patient-specific anatomical model using the personalized biomechanical model driven by the modulated patient-specific thoracic pressure force field.

24. The apparatus of claim 14, wherein the means for personalizing the biomechanical model for the patient by estimating a patient-specific thoracic pressure force field to drive the biomechanical model comprises:
- means for estimating the patient-specific pressure force field to drive the model from a plurality of images corresponding to a plurality of respiratory phases.

25. A non-transitory computer readable medium storing computer program instructions for predicting respiratory motion of a patient, the computer program instructions when executed by a processor cause the processor to perform operations comprising:
- generating a patient-specific anatomical model of the respiratory system from a 3D thoracic image of the patient;
- deforming the patient-specific anatomical model of the respiratory system using a biomechanical model;
- personalizing the biomechanical model for the patient by estimating a patient-specific thoracic pressure force field to drive the biomechanical model; and
- predicting respiratory motion of the patient using the personalized biomechanical model driven by the patient-specific thoracic pressure force field, wherein the patient-specific anatomical model includes at least one lung region, a thorax region, and a sub-diaphragm region, and generating the patient-specific anatomical model of the respiratory system from the 3D thoracic image of the patient comprises:
  - segmenting the at least one lung region, the thorax region, and the sub-diaphragm region in the 3D thoracic image;
  - generating a respective mesh for each of the segmented at least one lung region, thorax region, and sub-diaphragm region; and
  - defining a plurality of pressure zones on the meshes for the thorax region and the sub-diaphragm region.

26. The non-transitory computer readable medium of claim 25, wherein the operations further comprise:
- displaying a 3D+time respiratory motion map showing the predicted respiratory motion.

27. The non-transitory computer readable medium of claim 26, wherein the operations further comprise:
- performing one of image reconstruction or therapy delivery using the 3D+time respiratory motion map.

28. The non-transitory computer readable medium of claim 25, wherein defining a plurality of pressure zones on the meshes for the thorax region and the sub-diaphragm region comprises:
- defining pressure zones for the mesh of the thorax region by sub-dividing an inner surface of the thorax into a plurality of evenly spaced rings and splitting each ring into a plurality of pressure zones; and
- defining pressure zones for the mesh of the sub-diaphragm region by splitting a superior surface of the sub-diaphragm region into a plurality of zones.

29. The non-transitory computer readable medium of claim 25, wherein deforming the patient-specific anatomical model of the respiratory system using a biomechanical model comprises:
- deforming the meshes for the at least one lung region, thorax region, and sub-diaphragm region based on forces due to pressures applied to the plurality of pressure zones on the thorax mesh and the sub-diaphragm mesh and based on interaction forces between the thorax mesh, the sub-diaphragm mesh and the at least one lung mesh calculated using a collision model that models sliding interactions between the meshes.

30. The non-transitory computer readable medium of claim 29, wherein personalizing the biomechanical model for the patient by estimating a patient-specific thoracic pressure force field to drive the biomechanical model comprises:
- estimating pressures applied to the pressure zones of the thorax mesh and the sub-diaphragm mesh to deform the lung mesh from two images corresponding to a first respiratory phase and a second respiratory phase.

31. The non-transitory computer readable medium of claim 30, wherein estimating pressures applied to the pressure zones of the thorax mesh and the sub-diaphragm mesh to deform the lung mesh from two images corresponding to a first respiratory phase and a second respiratory phase comprises:
  (a) performing an optimization algorithm to estimate optimal pressures applied to a single pressure zone on the thorax mesh and a single pressure zone one the sub-diaphragm mesh with predetermined initial values of the pressures;
  (b) increasing a number of pressure zones on the thorax mesh and a number of pressure zones on the sub-diaphragm mesh;
  (c) performing the optimization algorithm to estimate optimal pressures applied to the increased number of pressure zones on the thorax mesh and the sub-diaphragm mesh using previously estimated optimal pressure values as initial values; and
  (d) repeating steps (b) and (c) until a target number of pressure zones on the thorax mesh and sub-diaphragm mesh is reached.

32. The non-transitory computer readable medium of claim 25, wherein generating a patient-specific anatomical model of the respiratory system from a 3D thoracic image of the patient comprises:
- generating a first patient-specific anatomical model from a first 3D thoracic image at a first respiratory phase; and
- generating a second patient-specific anatomical model from a second 3D thoracic images at a second respiratory phase.

33. The non-transitory computer readable medium of claim 32, wherein deforming the patient-specific anatomical model of the respiratory system using a biomechanical model comprises:

deforming the first patient-specific anatomical model from the first respiratory phase to the second respiratory phase using the biomechanical model.

34. The non-transitory computer readable medium of claim 33, wherein personalizing the biomechanical model for the patient by estimating a patient-specific thoracic pressure force field to drive the biomechanical model comprises:

comparing the deformed first patient-specific anatomical model with the second patient-specific anatomical model; and estimating a thoracic pressure force field that minimizes a cost function based on the comparison of the deformed first patient-specific anatomical model with the second patient-specific anatomical model.

35. The non-transitory computer readable medium of claim 34, wherein the first respiratory phase is an end-exhale (EE) phase and the second respiratory phase is an end-inhale (EI) phase.

36. The non-transitory computer readable medium of claim 25, wherein predicting respiratory motion of the patient using the personalized biomechanical model driven by the patient-specific thoracic pressure force field comprises:

modulating the patient-specific thoracic pressure force field; and deforming the patient-specific anatomical model using the personalized biomechanical model driven by the modulated patient-specific thoracic pressure force field.

37. The non-transitory computer readable medium of claim 25, wherein personalizing the biomechanical model for the patient by estimating a patient-specific thoracic pressure force field to drive the biomechanical model comprises:

estimating the patient-specific pressure force field to drive the model from a plurality of images corresponding to a plurality of respiratory phases.

* * * * *